(12) United States Patent
Simpson, Jr. et al.

(10) Patent No.: US 11,529,494 B1
(45) Date of Patent: Dec. 20, 2022

(54) CATHETER SUPPORT

(71) Applicant: Robert E. Simpson, Jr., Amhearst, MA (US)

(72) Inventors: Robert E. Simpson, Jr., Amhearst, MA (US); Dave Bacon, Keene, NH (US); Henry Gauthier, Brattleboro, VT (US); Richard L Kalich, Spofford, NH (US); Arthur F. Keating, Brownsville, VT (US); Peter Sucharzewsky, Claremont, NH (US)

(73) Assignee: Robert E. Simpson, Amherst, MA (US)

( * ) Notice: Subject to any disclaimer, the term of this patent is extended or adjusted under 35 U.S.C. 154(b) by 449 days.

(21) Appl. No.: 16/412,680

(22) Filed: May 15, 2019

Related U.S. Application Data

(62) Division of application No. 13/778,366, filed on Feb. 27, 2013, now Pat. No. 10,315,004.

(51) Int. Cl.
| | | |
|---|---|---|
| *A61M 25/00* | (2006.01) | |
| *A61M 25/02* | (2006.01) | |
| *A61F 5/453* | (2006.01) | |

(52) U.S. Cl.
CPC ......... *A61M 25/0017* (2013.01); *A61F 5/453* (2013.01); *A61M 25/02* (2013.01); *A61M 2025/0213* (2013.01); *A61M 2210/167* (2013.01)

(58) Field of Classification Search
CPC .. A61F 5/451; A61F 5/453; A61F 5/48; A61F 16/04; A61M 39/00; A61M 25/0017; A61M 25/02; A61M 2025/0213; A61M 2210/167
See application file for complete search history.

(56) References Cited

U.S. PATENT DOCUMENTS

| | | | | | |
|---|---|---|---|---|---|
| 1,032,611 | A | * | 7/1912 | Keyes ................. | A61M 25/02 604/179 |
| 3,742,953 | A | * | 7/1973 | Lee ..................... | A61F 5/453 604/352 |
| 4,419,097 | A | * | 12/1983 | Rowland ............ | A61M 25/02 604/174 |
| 4,571,241 | A | * | 2/1986 | Christopher ........ | A61M 25/04 D24/112 |
| 4,810,247 | A | * | 3/1989 | Glassman ........... | A61F 5/453 604/174 |

(Continued)

*Primary Examiner* — Nicholas J. Weiss
*Assistant Examiner* — Gabriella E Burnette
(74) *Attorney, Agent, or Firm* — Joanne M. Martin

(57) ABSTRACT

A catheter support comprising a pliant tubular structure of rigidity greater than the penis including a region surrounding the penis shaft, a region surrounding the penis head, and a substantially closed end having an aperture aligned with the penis terminal opening through which the catheter is received. The catheter support limits or eliminates catheter movement substantially radial to the axis of the catheter and thus radially against the inner opening if the penis head, substantially reducing or eliminating abrasion or other insult to the penis surfaces and tissue that interface with the catheter. One embodiment comprises 2 substantially identical elongated halves having longitudinal recesses and hinged together to close around the penis end and catheter providing the catheter support in a structure having improved comfort and wearability.

5 Claims, 5 Drawing Sheets

(56) References Cited

U.S. PATENT DOCUMENTS

| | | | | |
|---|---|---|---|---|
| 5,078,707 A | * | 1/1992 | Peter Klug | A61F 5/453 604/349 |
| 5,423,784 A | * | 6/1995 | Metz | A61F 5/453 604/351 |
| 6,248,096 B1 | * | 6/2001 | Dwork | A61F 5/453 604/347 |

* cited by examiner

CATHETER SUPPORT

The present application claims priority of and is a divisional application of previously filed co-pending application Ser. No. 13/788,366 filed 27 Feb. 2013, a divisional application of application Ser. No. 12/928,738, U.S. Pat. No. 8,500,719 filed 20 Dec. 2010 for CATHETER SUPPORT.

FIELD OF THE INVENTION

The present invention relates to supports for catheters introduced into the body, in particular, to supports for catheters introduced into the penis.

BACKGROUND OF THE INVENTION

The penis, having its unique structure, functions and tissue is in general unwelcoming to catheters and the rigid mechanical catheter supports. While having some minor degree of rigidity, relative to catheters inserted therein, the penis is relatively flaccid and further includes soft, sensitive and delicate tissues at its terminal end. Moreover, at this terminal end with the entering catheter, most discomfort is experienced by the wearer.

Attempts to alleviate discomfort by inserting a sleeve within the initial penis opening much like a catheter introducer ultimately becomes more uncomfortable than the catheter itself, and often cannot be worn for the needed duration. Other external rigid structures are generally unwearable or cannot be reliably supported by the penis, while flexible and very pliant structures may not provided the needed catheter support.

SUMMARY OF THE INVENTION

The catheter support according to the present invention comprises a pliant tubular structure of rigidity greater than the penis including a region surrounding the penis shaft, a region surrounding the penis head, and a substantially closed end having an aperture aligned with the penis terminal opening through which the catheter is received. The catheter support limits or eliminates catheter movement substantially radial to the axis of the catheter and thus radially against the inner opening if the penis head, substantially reducing or eliminating abrasion or other insult to the penis surfaces and tissue that interface with the catheter.

One embodiment comprises 2 substantially identical elongated halves having longitudinal recesses and hinged together to close around the penis end and catheter providing the catheter support in a structure having improved comfort and wearability.

Further design embodiments accommodate variations in application.

BRIEF DESCRIPTION OF THE DRAWING

These and further features of the present invention will be better understood by reading the following Detailed Description together with the Drawing, wherein.

DETAILED DESCRIPTION

Figure 1:
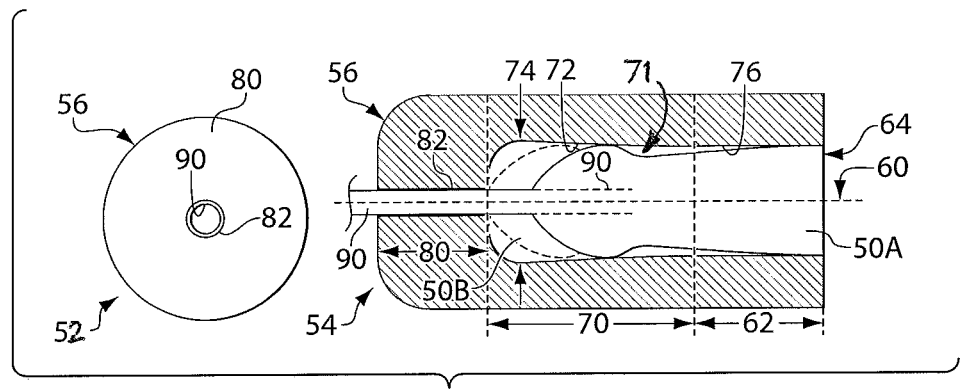
FIG. 1 is an end view and a cross-sectional view of one embodiment according to the present invention.

An end view 52 and a cross section view 54 of a first embodiment of the present invention is shown in FIG. 1 and is a substantially tubular outer structure 56 having a first section 62 with an opening 64 into the outer structure 56. The first section 62 opening 64 is typically symmetrical about a longitudinal axis extending the length of the outer structure 56, and has a substantially uniform opening throughout the length of the opening 64 and is sized to lightly grip the shaft portion of a penis. The embodiment of the present invention shown provides some movement of the penis relative to the outer structure 56 and is shown in a rearward position 50A as well as a maximally forward position 50B and typically assumes a position between the forward and rearward positions. In one embodiment, the first section is approximately 1" in length having an opening diameter of 0.75", and a wall 66 thickness of about 0.187".

A second section 70 of the outer structure also has an opening 72 that aligns with the opening 64, gradually expands from the opening 64 diameter to a larger diameter 74, and is substantially symmetrical about the axis 60. In one embodiment, the larger diameter 74 is about one-eight larger than opening 62, which approximately 0.85", and the second section axially extends approximately 1.25" from the first section 62. The second section 70 has a wall 76 of thickness typically diminishing from the wall thickness, and has an opening 72 typically has a rounded interior end distal from the first section 62 which is seen as a rapidly diminished diameter, at which point a third section 80 begins. The second section is typically dimensioned to retain and enclose the penis head.

In the embodiment of FIG. 1, the third section 80 has a substantially reduced diameter opening 82 typically sized to receive a catheter therethrough, the third section 80 having a substantially thicker wall than the second region, and disposed to limit or eliminate catheter movement of a catheter received therein, and catheter movement substantially radial to the axis 60 of the catheter and thus radially against the inner opening of the penis head, and providing a slight additional margin around the catheter to permit catheter insertion and/or retention without binding or pulling on the catheter 90 inserted into the opening 82. In this embodiment, the opening 82 is substantially uniform in diameter along the axis 60, and is typically centered around the axis 60. An opening 82 in one embodiment is 0.185" through a third section length of 0.75".

Figure 2:
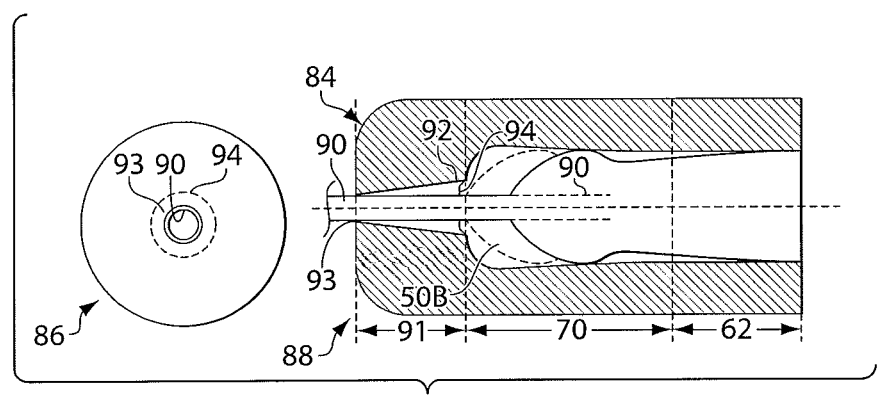
FIG. 2 is an end view and a cross-sectional view of an alternate embodiment according to the present invention.

A second embodiment of the present invention shown in FIG. 2 by an end view 86 and a cross section view 88 and is has a substantially tubular outer structure 84 having a first section 62 and second section 70 substantially the same as provided by the prior embodiment of FIG. 1. The second embodiment includes a third section 90 substantially the same as the third section 80 of the prior embodiment of FIG. 1, except that the longitudinal or axial opening 90 is non-uniform, and as shown in FIG. 2, tapers from a minimum opening end 93 to a maximum opening end 94 (proximal the penis head). In one embodiment, the minimum opening end 93 is slightly larger than the catheter 90, e.g. approximately $\frac{3}{16}$" for a 14 French catheter, and the maximum opening 94 expands amounts up to at least 100 percent of the minimum opening.

Figure 3:
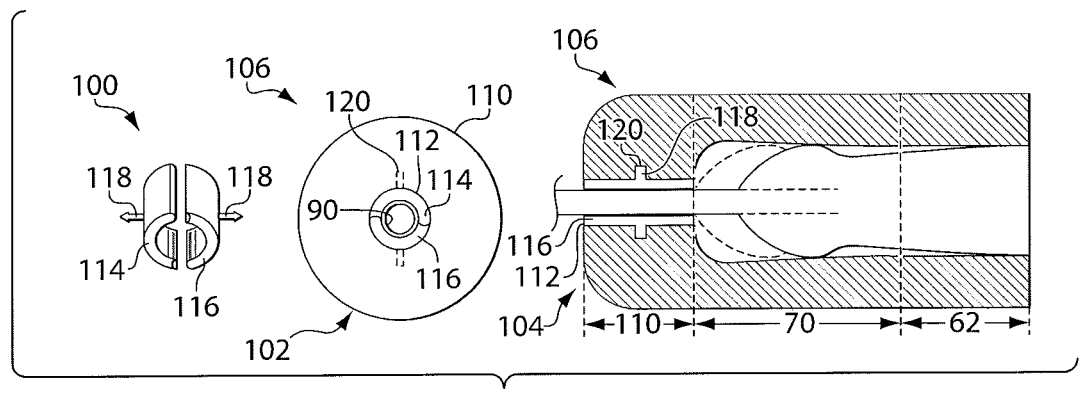
FIG. 3 is an end view and a cross-sectional view of an further alternate embodiment according to the present invention.

A third embodiment of the present invention shown in FIG. 3 by an end view 102 and a cross section view 104 and is has a substantially tubular outer structure 106 having a first section 62 and second section 70 substantially the same as provided by the prior embodiment of FIG. 1. The third embodiment includes a third section 110 substantially the same as the third section 80 of the prior embodiment of FIG. 1, except that the longitudinal or axial opening 112 is enlarged and receives a sleeve 100 into the enlarged opening 112. The sleeve 100 can be a single element having a cylindrical opening to receive the catheter 90, or a multi-sectioned element as shown, with 2 (or more) mating pieces 114, 116, which in the embodiment shown in FIG. 3, includes members 118 which extend radially outward from the mating pieces 114, 116 and each engage a corresponding recess 120 extending radially from the opening 112 in the third section 110.

Figure 4:
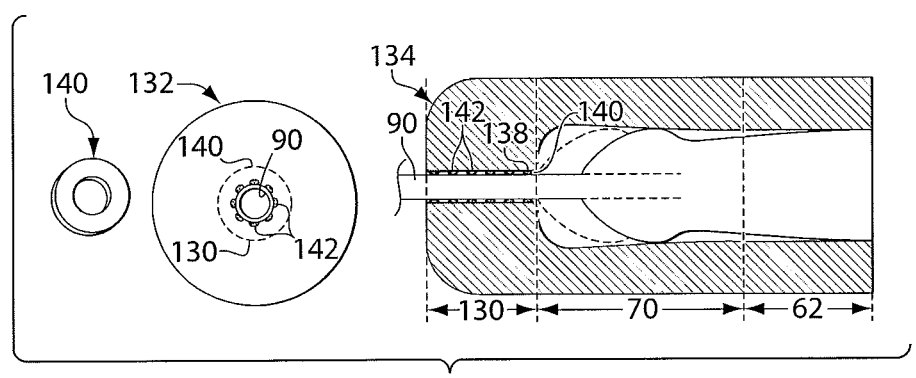
FIG. 4 is an end view and a cross-sectional view of a further alternate embodiment according to the present invention.

A fourth embodiment of the present invention shown in FIG. 4 by an end view 132 and a cross section view 134 and is has a substantially tubular outer structure 84 having a first section 62 and second section 70 substantially the same as provided by the prior embodiment of FIG. 1.

In the embodiment of FIG. 4, the third section 80 has a substantially reduced diameter opening 138 typically sized to receive a catheter therethrough, and providing a slight additional margin around the catheter to permit catheter insertion and/or retention without binding or pulling on the catheter 90 inserted into the opening 138, and to accommodate a lubricant, e.g. a dry, PTFE, etc. lubricant between the catheter 90 and the opening 138 surface. In this embodiment, the opening 138 is substantially uniform in diameter along the axis 60, and is typically centered about the axis 60. An opening in one embodiment is 0.185" through a third section length of 0.75" A further embodiment includes a washer 140 having an inner opening sized to permit the catheter to pass through yet small enough to urge the lubricant to be retained in the opening 138 without restricting movement of the catheter 90.

A typical use of the embodiments FIGS. 1-4 is to insert the catheter 90 into the head of the penis a desired amount and then to apply the embodiments of FIGS. 1-4 around the penis either by guiding the formed outer structure over the penis, or if comprising multiple section, carefully closing the outer structure over the penis.

Figure 5:
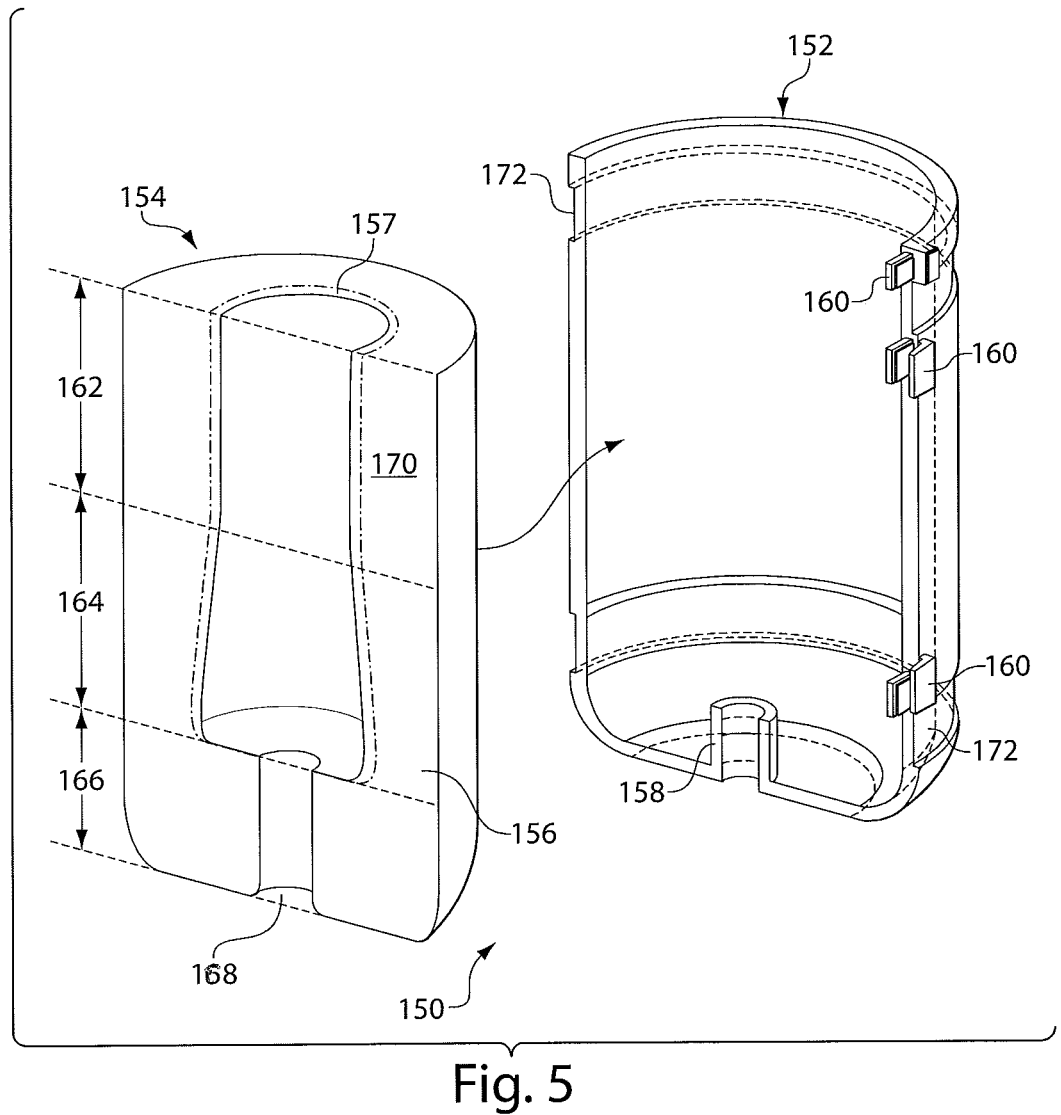
FIG. 5 is an exploded perspective view of a further alternate embodiment according to the present invention.

A further alternate embodiment 150 is shown in FIG. 5, comprising two longitudinal halves, each having a relatively rigid outer shell 152 which substantially surrounds and retains a resilient insert 154. Typically, the insert 154 comprises a softer material 154 such as foam, and are shaped to proved a sequence of longitudinal openings within sections 162, 164 and 166 of the insert to accommodate the penis shaft, the penis head and the catheter with a corresponding sequence of inner axially aligned openings of appropriate diameters, which in one embodiment corresponds to the openings sections 62, 70 and 80 of the embodiment of FIG. 1, and have wall 170 thickness defined by the section openings and the shell 152 inner dimensions. In one embodiment, the insert 154 comprises a flexible foam to allow for body changes and a compression grip about the penis shaft and/or head. Moreover, the insert implementation of the present invention provide low-cost accommodation of various penis sizes by correspondingly dimensioned inner openings with different pairs of inserts 154 while maintaining the same outer shell 152. Alternate embodiments of this and other embodiments include a polypropylene or other water absorbing or water-wicking layer 157 disposed to be in contact with the penis, or porous foam 156 and/or shell 152, or equivalent in the other embodiments of the present invention. An optional shell inner extension 158 extends into the insert recess 168 and into which the catheter is initially inserted. Typically the shells 152 mate and include a means to secure the shells 152 together such as clips 160 which engage corresponding portions or recesses in the typically identical mating shell (not shown). Alternately, the shells (and inserts therein) can be secured together with encircling elements (not shown) and a recess 172 may be included within the periphery of the shell 152.

Figure 6:
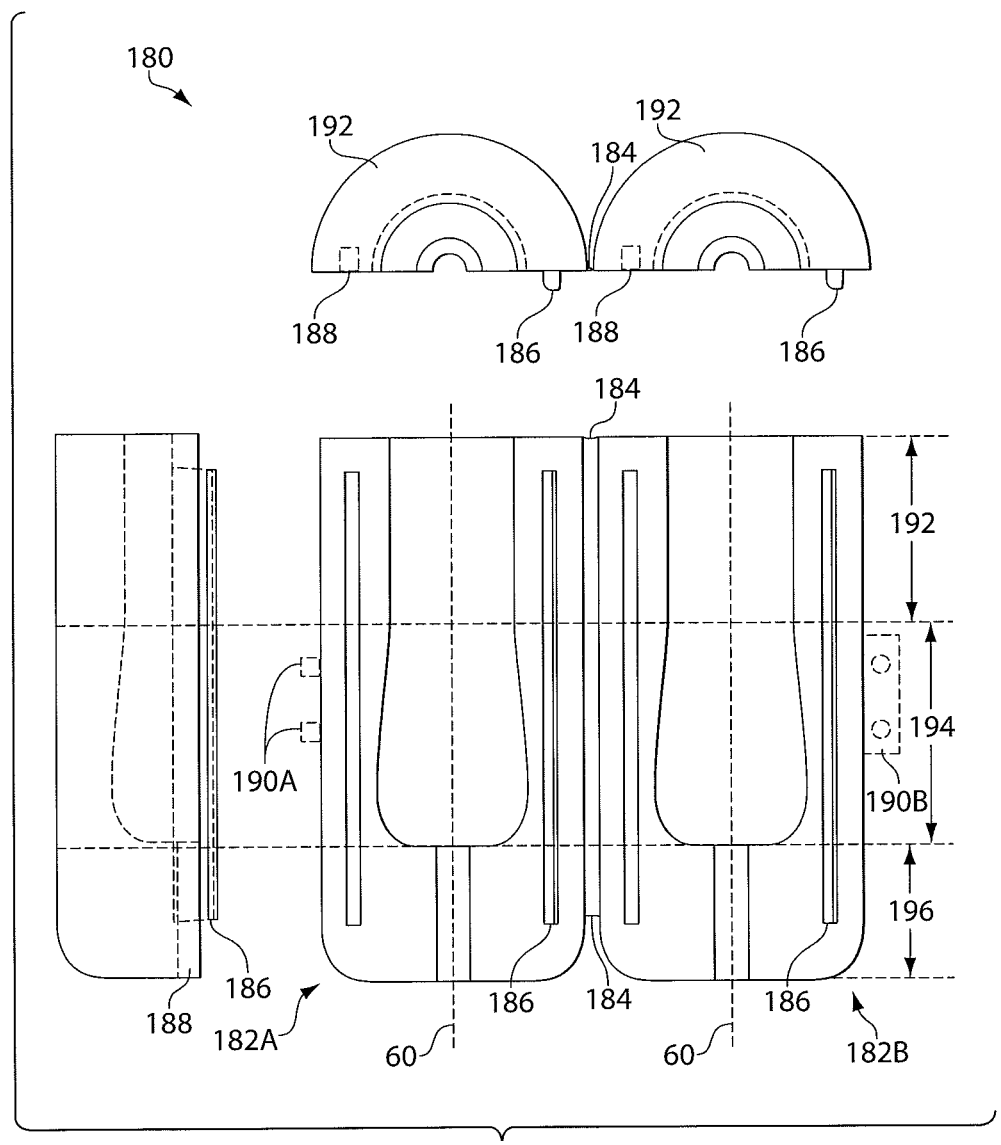
FIG. 6 is side, end and plan view of a further alternate embodiment according to the present invention.

A further embodiment 180 is shown in FIG. 6, wherein the catheter support comprises a pair of mating pieces or members comprising a first elongated enclosure and a second elongated enclosure 182A, 1826, each of said first elongated enclosure and said second elongated enclosure being elongated and mating on a plane substantially including the axis and when mated form a tubular structure (also shown in FIGS. 1-4) having a substantially uniform outer diameter along its length, and are connected by a hinge 184. In the embodiment shown the catheter support 180 includes 3 axially contiguous regions 192, 194 and 196 having inner openings substantially axially aligned, and may comprise the dimensions of the corresponding openings 64, 72 and 82 as may be proportioned to the anticipated penis dimensions. To guide the closing together of the mating catheter support pieces 182A, 182B about the hinge 184, ridge guides 186 and complementary mating ridge guide recesses 188 are formed and positioned to receive the corresponding guide elements from the other of the mating pieces. In the Instant embodiment, they are longitudinally disposed on the divided wall edge of the catheter holder 180 parallel to the axis 60, and the 3 axially contiguous regions comprise a sequence of contiguous regions of selected diameters, including a first region comprising a substantially uniform interior diameter along the axis and has an external opening into said mated pair of members, a second region communicating with the first region and comprising a gradually increasing interior diameter with increasing distance from the first region providing a rounded interior end distal from the first region and having a distal end diameter diminished from the gradually increased diameter, and a third region communicating with the second region and comprising a diminished interior diameter substantially less than the region interior diameter and having a substantially thicker wall than the second region, and disposed to limit or eliminate catheter movement of a catheter received therein, and catheter movement substantially radial to the axis 60 of the catheter and thus radially against the inner opening of the penis head, wherein the first region, the second region, and the third region are axially aligned. In addition to the closure devices previously discussed regarding other embodiments and applied hereto, still further closure devices 190A, 190B or as may be known in the art may be applied to the embodiment of the resent invention. Closure devices applicable to this and other embodiments include tape, snaps, Velcro™, buttons and/or clasps.

A typical use of the embodiments FIGS. 5 and 6 is to insert the catheter 90 into the head of the penis a desired amount and then to apply the embodiments of FIGS. 5 and 6 around the penis either by guiding the formed outer structure over the penis, or if comprising multiple section, carefully closing the outer structure over the penis.

Figure 7:
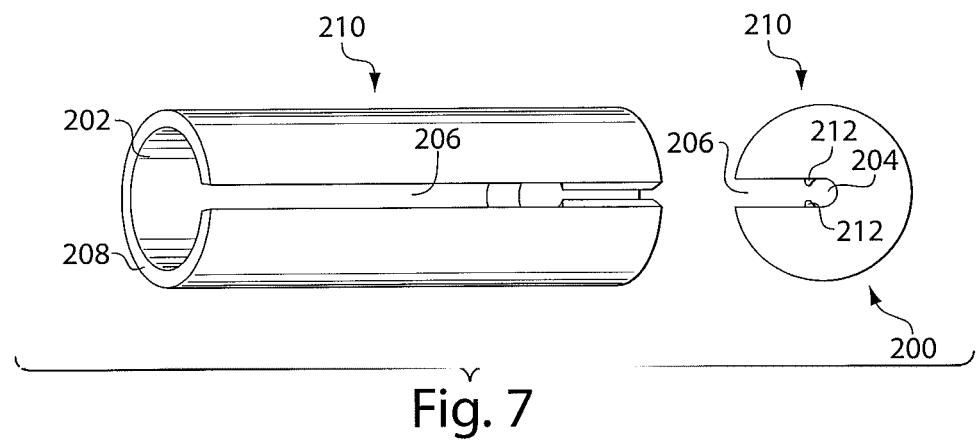
FIG. 7 is a side perspective and end view of a further alternate embodiment according to the present invention.
Figure 8:
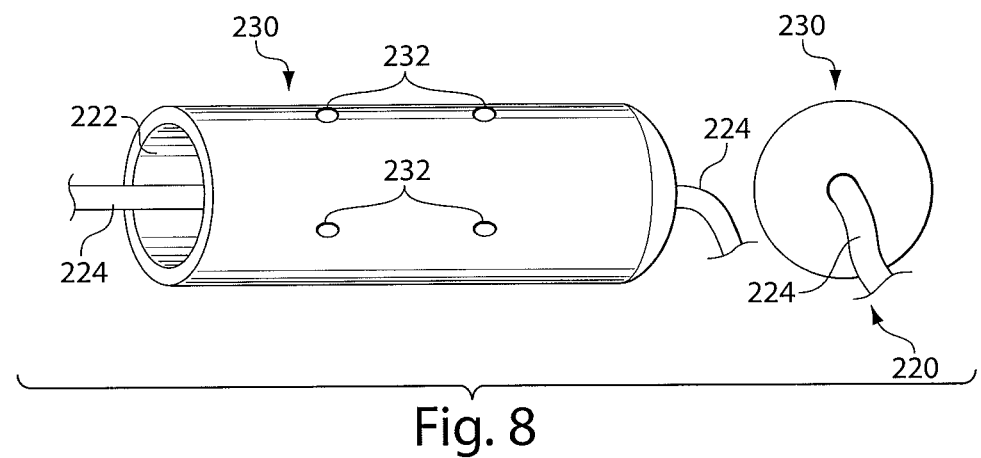
FIG. 8 is a side perspective and end view of a further alternate embodiment according to the present invention.

The further alternate embodiment 200 of FIG. 7 comprises a tubular member 210 having an opening 202 at one end sized to receive the penis head and shaft and a smaller opening 204 at the opposite end of the tubular member 210 through which a catheter (not shown) is received and supported as described in the above embodiments. The tubular member 210 includes a slot 206 extending along the wall of the tubular member 210 (including slot in each of a penis shaft support, a penis head support and a catheter support as describe in the above embodiments aligned or otherwise in communication) from the opening into which the penis is received, to the smaller opening 204 and through which the catheter may be moved and ultimately be place through the smaller opening 204 and into the center of the tubular member 210. The slot 206 and other slots (not shown) extending along a smaller portion of the length of the tubular member may provide ventilation or air movement and mitigate the build-up of moisture, and such slots are applicable to other embodiments shown herewith. The embodiment may also include a slot 206 with walls 208 and raised portions (or other mechanism) which urges the catheter to remain in the smaller opening 204. Alternate embodiment provide a resilient tubular member having adhesive disposed on the slot walls 208 permitting all or portions of the slot to be closed around the penis.

A further alternate embodiment 220 according to the present invention comprising a tubular member 230 having a opening 222 disposed at one end of the tubular member into the penis shaft and penis head is received and a smaller opening at the opposite end of the tubular member through which a catheter 224 passes (and is supported as provided with the above embodiments) and forms an assembly together with the tubular member 230. This embodiment (and other above embodiments) may further include apertures 228 disposed along the length of the tubular member extending inward to provide a ventilation passageway providing a flow of air proximal or in contact with the penis (or internal moisture controlling layers, e.g. 157 of FIG. 5) to reduce moisture or heat (or both) within the embodiments of the present invention.

Figure 9:
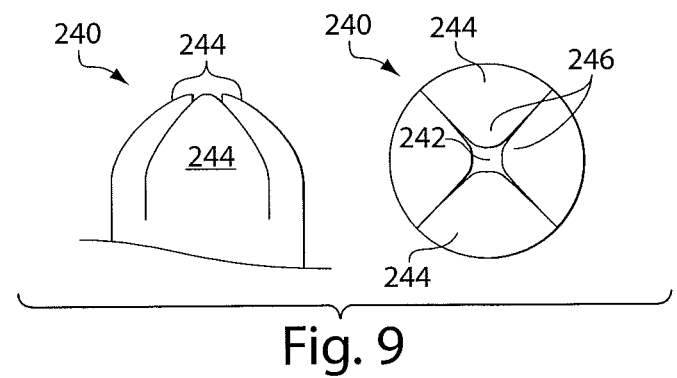
FIG. 9 is a partial side view and an end view of a further alternate embodiment according to the present invention.

A further alternate embodiment 240 is shown in FIG. 9, wherein the catheter support end of tubular member, also receiving the penis shaft and penis head in an opposite end opening, comprises several sections 244 extending radially outward from the catheter support end opening 242. The section 244 tips 246 converge but stop short and form the opening 242 through which the catheter passes, and may comprise the thickness necessary for catheter support as described for the above embodiments or may merely provide a sufficiently rigid outer structure to protect and support the catheter from moving radially against the head of the penis as radial or other forces are applied to the catheter outside the catheter support, having a thickened insert material therebehind to provide the above described catheter support.

The embodiments provided herein are understood to be exemplary and the scope of the present invention is not limited thereto. Modifications and substitutions as may be known to one of ordinary skill in the art are included herewith. The scope of the claims is not limited except by the claims that follow.

What is claimed is:

1. An apparatus, comprising: a pair of mating members comprising a first elongated enclosure and a second elongated enclosure, each of said first elongated enclosure and said second elongated enclosure being elongated and mating along an axis, when mated form a tubular structure having a substantially uniform outer diameter along the pair of mating members length including an aperture therein aligned with said axis and having a sequence of contiguous regions of selected diameters, including a first region comprising a substantially uniform interior diameter along said axis and has an external opening into said pair of mating members, a second region communicating with said first region and comprising a gradually increasing interior diameter with increasing distance from said first region providing a rounded interior end distal from said first region and having a distal end diameter diminished from said gradually increased diameter, and a third region communicating with said second region and comprising a diminished interior diameter substantially less than said first region interior diameter and having a substantially thicker wall than the second region, and disposed to limit catheter movement substantially radial to the axis of a catheter received therein and engaging said diminished interior diameter, and limit catheter movement radially against the inner opening of the penis head, wherein said first region, said second region, and said third region are axially aligned.

2. The apparatus of claim 1, wherein subsequent to increasing in diameter away from said first region, said second region interior diameter is reduced proximal said third region.

3. The apparatus of claim 1, wherein said third region includes a sleeve having said third region interior diameter formed therein.

4. The apparatus of claim 1, wherein at least a portion of said third region interior diameter is sized to receive a catheter therethrough and having a length greater than said third region portion interior diameter.

5. The apparatus of claim 4, wherein said third region portion interior diameter is tapered to provide a diminished diameter distal from said second region.

* * * * *